May 1, 1962 H. C. SWIM ETAL Plant Pat. 2,143
ROSE PLANT
Filed April 12, 1961
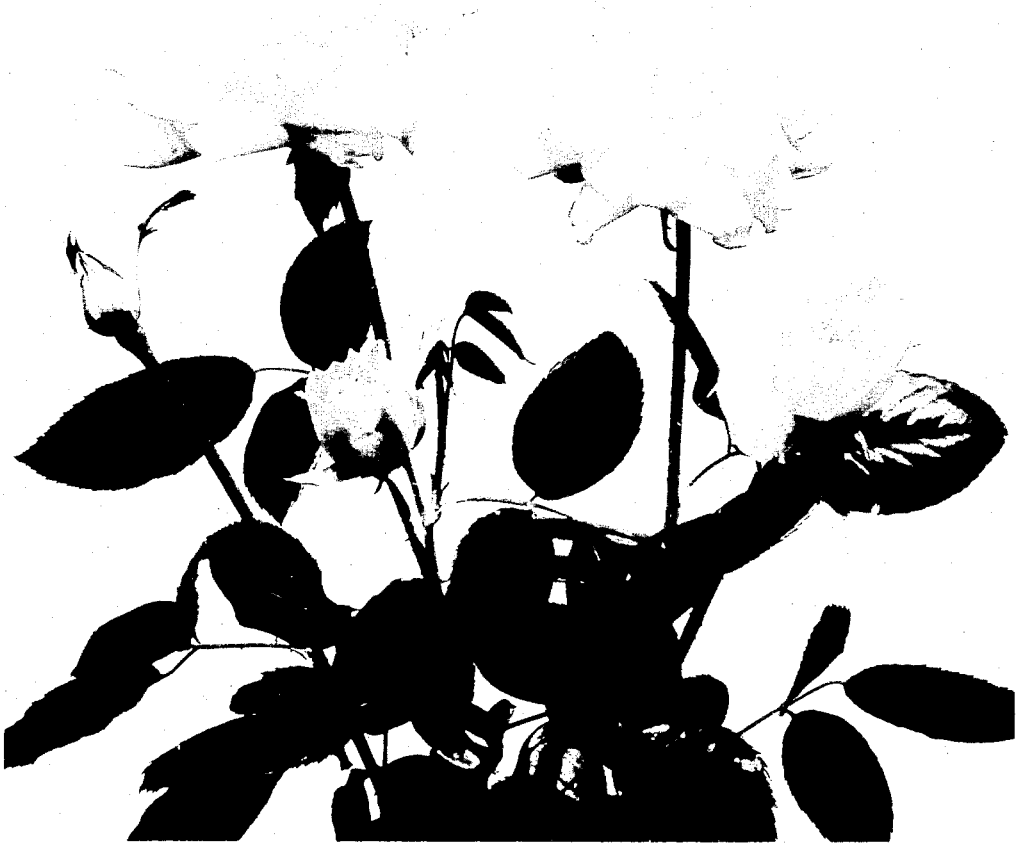
INVENTORS
H. C. Swim
O. L. Weeks
BY Robb & Robb
ATTORNEYS United States Patent Office Plant Pat. 2,143
Patented May 1, 1962

2,143
ROSE PLANT

Herbert C. Swim, Ontario, and O. L. Weeks, Chino, Calif., assignors to C. R. Burr and Company, Inc., Manchester, Conn., a corporation of Connecticut Filed Apr. 12, 1961, Ser. No. 102,618
1 Claim. (Cl. 47—61)

The present invention relates to a new and distinct variety of rose plant of the hybrid tea class, which was originated by us by crossing the variety "Charlotte Armstrong" (Plant Patent No. 455) with the variety "Signora" (Plant Patent No. 201).

As the result of this breeding, we have produced a new rose variety which is endowed with the following unique combination of characteristics which are outstanding therein and which distinguish it from its parents, as well as from all other varieties of which we are aware:

(1) An unusual uniformity, abundance and vigor of the canes;

(2) Very large, abundant, glossy and flat foliage;

(3) A substantially greater quantity of buds and flowers, as compared with other varieties in the orange flower color range;

(4) A substantially greater flower petalage, as compared with most other varieties in the orange flower color range; and (5) A distinctive, attractive and smooth orange color of the flowers and buds, with a pencilling of yellow color around the margins of the petals.

In comparison with its said parent "Charlotte Armstrong," the habit of growth of the new variety is more upright, instead of upright-spreading in the case of this parent; the foliage of the new variety is glossy, as contrasted with the non-glossy foliage of this parent; the buds of the new variety are short-ovoid, rather than long-pointed to urn-shape as in the case of this parent; and the color of the buds and flowers of the new variety falls in the general category of orange as distinguished from the blood red to cerise color of the flowers of "Charlotte Armstrong."

As compared with its pollen parent "Signora," the canes of the new variety are more uniform in caliper than those of this parent; the new variety is clothed with a substantially greater abundance of foliage; the new variety is substantially more floriferous than "Signora" when grown under comparable conditions in southern California; and the buds and flowers of the new variety are a smooth orange color, as distinguished from the multi-colored flowers of "Signora" in which the buds and flowers range through the several colors yellow, orange, red and pink.

Asexual reproduction of our new variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Maryland, except where general color terms of ordinary dictionary significance are obvious:

Type: Tall; bush; outdoor; seedling; for cut flowers and for garden decoration.

Class: Hybrid tea.

Breeding: Seedling.

*Seed parent.*—"Charlotte Armstrong."

*Pollen parent.*—"Signora."

Propagation: Holds its distinguishing characteristics through succeeding propagations by budding.

*Flower*

Locality where grown and observed: Chino, California.

Flowers borne: Singly; on long stems of a strength ranging from normal to strong.

Quantity of bloom: From free to abundant, both outdoors and in greenhouse.

Continuity: From intermittent to continuous.

Fragrance: Moderate. Nature—tea.

Bud:

*Peduncle.*—Long; heavy; erect; stiff; rough; with numerous hairs and prickles. Color—medium yellowish green.

*Before calyx breaks.*—Size—large. Form—pointed; with foliaceous appendages on the surface of the bud; with slender foliaceous parts extending beyond the tip of the bud equal to ¾ or more of its length. Color—near Moderate Yellow Green, Plate 7.5GY 5/7.

*As calyx breaks.*—Color—near Strong Yellowish Pink, Plate 10R 7/9, faintly veined with yellow.

*As first petal opens.*—Size—medium. Form—short; pointed. Color: outside—near Moderate Orange-Yellow, Plate 10YR 8/10 at base and radiating from point of attachment to near margin of petal, with remainder of petal suffused with Strong Yellowish Pink, Plate 10R 7/9, except at edge where there is a pencilling of Moderate Orange Yellow, Plate 10YR 8/10; inside—base of Vivid Yellow, Plate 2.5Y 8/12 to Brilliant Yellow, Plate 2.54Y 9/9 in area 1/4 inch around point of attachment, blending with Strong Yellowish Pink, Plate 7.5R 7/9 in diminishing degree approaching margin where latter color completely dominates except for pencilling of Moderate Orange Yellow, Plate 10YR 8/10 at edge. Opening—opens up well.

Bloom:

*Size (when fully open).*—From medium to large; from 4 inches to 5½ inches.

*Petalage.*—From double to very double; from 35 to 45 petals; arranged regularly, but with from 10 to 25 petaloids in center arranged irregularly.

*Form.*—Flat at first, but becoming high-centered; petals at first being somewhat loosely rolled inward, but later becoming very loosely erect at maturity.

Petals:

*Texture.*—Medium thick; medium soft. Inside—satiny. Outside—from shiny to satiny.

*Shape.*—Outside—nearly round, with apex only very slightly acute. Intermediate—obovate, with apex very slightly acute. Inside—obovate-lanceolate, with apex slightly acute.

This description of a newly opened flower was made from a rose grown in a greenhouse during the month of January at Chino, California:

*Color.*—Outer petal: outside surface—near Moderate Orange Yellow, Plate 10YR 8/10 at base and radiating from point of attachment to near margin of petal, with remainder of petal suffused with Strong Yellowish Pink, Plate 10R 7/9, except at edge where there is a pencilling of Moderate Orange Yellow, Plate 10YR 8/10; inside surface—base Vivid Yellow, Plate 2.5Y 8/12, to Brilliant Yellow, Plate 2.5Y 9/9 in area ¼ inch around point of attachment, blending with Strong Yellowish Pink, Plate 7.5R 7/9 in diminishing degree approaching margin where latter color completely dominates except for pencilling of Moderate Orange Yellow, Plate 10YR 8/10 at edge, with Moderate Orange Yellow, Plate 10YR 8/10 sometimes following midrib of petal for about ½ of its length. Intermediate petal: outside surface—Brilliant Yellow, Plate 2.5Y 9/9 over about ⅓ of basal portion of petal and radiating in vein-like pattern over remainder of petal and becoming faint at margin, with color between veining near Moderate Yellowish Pink, Plate 7.5R 8/6, except at edge where there is pencilling of Brilliant Yellow, Plate 2.5Y 9/9; inside surface—base Vivid Yellow, Plate 2.5Y 8/12 to Brilliant Yellow, Plate 2.5Y 9/9, blending with red to form Strong Orange, Plate 2.5YR 7/10, succeeded by Strong Yellowish Pink, Plate 7.5R 7/9, with pencilling of brilliant Yellow, Plate 2.5Y 9/9 at edge. Inner petal: outside surface—Brilliant Yellow, Plate 5Y 9/9 over approximately ½ of basal portion, blending with faint red to form Moderate Yellowish Pink, Plate 7.5R 8/6 over most of upper half of petal, with edge pencilled with Brilliant Yellow, Plate 5Y 9/9; inside surface—base Vivid Yellow, Plate 2.5Y 8/12 to Brilliant Yellow, Plate 2.5Y 9/9, blending with red to form Strong Orange, Plate 2.5YR 7/10, succeeded by Strong Yellowish Pink, Plate 7.5R 7/9, with pencilling of Brilliant Yellow, Plate 2.5Y 9/9 at edge.

This description was made from a rose that was open for three days in a greenhouse during the month of January at Chino, California:

*Color.*—Outer petal: outside surface—Brilliant Greenish Yellow, Plate 7.5Y 9/8 at basal third of petal, with this color following midrib to margin and radiating veins to very near margin, with area between veins Light Yellowish Pink, Plate 7.5R 9/3; inside surface—from Brilliant Yellow, Plate 5Y 9/9 to Bright Greenish Yellow, Plate 7.5Y 9/8 in small area at base, becoming from Light Orange, Plate 5YR 8/7 to Light Yellowish Pink, Plate 2.5YR 9/3 in central portion and giving way to Light Yellowish Pink, Plate 7.5R 9/3 at outer portion of petal. Inner petal: outside surface—Brilliant Greenish Yellow, Plate 7.5Y 9/8 at basal third of petal, gradually giving way to Pale Pink, Plate 2.5R 9/3 over upper and outer portion; inside surface—from Brilliant Yellow, Plate 5Y 9/9 to Bright Greenish Yellow, Plate 7.5Y 9/8 in small area at base, gradually replaced by Pale Pink, Plate 2.5R 9/3 over remainder of petal.

*General color effect.*—Newly opened flower—between Strong Yellowish Pink, Plate 7.5R 7/9 and Strong Reddish Orange, Plate 7.5R 6/12. 3-days open—near Moderate Yellowish Pink, Plate 10R 8/6.

*Behavior.*—Usually drop off cleanly; old petals hang on after rain or extreme heat.

*Flower longevity.*—Cut roses grown in greenhouse and kept at living-room temperatures—4 days in January.

*Reproductive Organs*

Stamens: Medium number; arranged irregularly about pistils; mixed with petaloids; tucked in calyx.

Filaments: From short to medium length; most with anthers. Color—yellow.

Anthers: From small to medium size; all open at once. Color—yellow.

Pollen: From moderate quantity to abundant. Color—yellow.

Pistils: Medium number.

Styles: From short to medium length; from thin to medium caliper; loosely bunched.

Stigma: Color—yellow.

Ovaries: Mostly enclosed in, but some protruding from, calyx.

Hips: Globular; hairy; glandular; walls thick and fleshy; somewhat small for this class.

Sepals: Permanent; long; curled.

Seeds: Few; medium size.

*Plant*

Foliage:

*Leaves.*—Compound of 3 to 5 leaflets; abundant; very large; glossy; flat.

*Leaflets.*—Shape—lanceolate, with apex acute. Base—round. Margin—both simply and doubly serrate.

*Color.*—Mature: upper surface—between Dark Yellowish Green, Plate 10GY 4/5 and Moderate Olive Green, Plate 7.5GY 4/4; under surface—a grayed hue of light yellowish green that is not comparable with any available chart color. Young: upper surface—near Moderate Yellow Green, Plate 2.5GY 5/5, somewhat influenced by veining and netting of Dark Purplish Red, Plate 10RP 3/10; under surface—near Strong Yellow Green, Plate 2.5GY 6/8, very strongly influenced by veining and netting of Dark Purplish Red, Plate 10RP 3/10.

*Rachis (the supporting stem of the compound leaf).*—From light to medium thickness. Upper side—grooved; glandular. Under side—sparsely prickly; slightly glandular.

*Stipules.*—Short; adnate; moderately narrow; with short points turning out at an angle of 45°.

*Disease resistance.*—Better than average resistance to powdery mildew, as compared with other varieties grown under comparable cultural conditions at Chino, California.

Growth:

*Habit.*—Bushy; upright; much-branched.

*Growth.*—Vigorous.

*Canes.*—Medium caliper.

*Main stems.*—Color—from green to brown. Large prickles—many; medium length; slightly hooked downward; with short, broad base; color—brown. Small prickles—few; color—brown. Hairs—none.

*Branches.*—Color—green. Large prickles—many; medium length; slightly hooked downward; with short, broad base; color—brown. Small prickles—few; color—brown. Hairs—none.

*New shoots.*—Color—bronze-red. Large prickles—several; medium length; straight; with short, broad base; color—green, with anthocyanin at base. Small prickles—few; color—reddish at base. Hairs—none.

We claim:

A new and distinct variety of rose plant of the hybrid tea class, substantially as herein shown and described, characterized particularly as to novelty by the unique combination of unusual uniformity, abundance and vigor of the canes, very large, abundant, glossy, and flat foliage, a substantially greater than normal quantity of buds and flowers and a substantially greater flower petalage in comparison with the flowers of other varieties of the orange color range, and a distinctive, attractive and smooth orange color of the flowers, with pencillings of yellow around the margins of the petals.

No references cited.